United States Patent [19]

Hamprecht et al.

[11] 4,327,034
[45] Apr. 27, 1982

[54] SULFAMIC ACID HALIDES AND PROCESSES FOR THE PREPARATION OF SULFAMIC ACID HALIDES

[75] Inventors: Gerhard Hamprecht, Weinheim; Adolf Parg, Bad Durkheim; Karl-Heinz Koenig, Frankenthal, all of Fed. Rep. of Germany

[73] Assignee: BASF Aktiengesellschaft, Fed. Rep. of Germany

[21] Appl. No.: 51,743

[22] Filed: Jun. 25, 1979

[30] Foreign Application Priority Data

Jul. 1, 1978 [DE] Fed. Rep. of Germany ....... 2828969
Mar. 23, 1979 [DE] Fed. Rep. of Germany ....... 2911456

[51] Int. Cl.$^3$ .................... C07C 155/02; C07C 79/44; C07C 143/12; C07C 125/06
[52] U.S. Cl. ........................... 260/455 A; 260/455 R; 260/543 R; 260/543 F; 260/948; 560/125; 560/149; 560/115; 560/145; 560/148
[58] Field of Search ........... 260/455 R, 455 A, 543 R, 260/543 F, 948; 560/125, 149, 115, 145, 148

[56] References Cited

U.S. PATENT DOCUMENTS

| | | | |
|---|---|---|---|
| 2,079,541 | 5/1937 | Battegay | 260/543 R |
| 2,891,065 | 6/1959 | Gündel | 260/455 A |
| 3,869,509 | 3/1975 | Kuhle et al. | 260/543 R |
| 4,014,904 | 3/1977 | Fischer et al. | 260/543 R |
| 4,014,931 | 3/1977 | Hamprecht | 260/543 R |
| 4,071,351 | 1/1978 | Arneklev et al. | 560/148 |
| 4,113,939 | 9/1978 | Fischer et al. | 260/453 R |
| 4,131,620 | 12/1978 | Hamprecht | 260/543 R |

FOREIGN PATENT DOCUMENTS

| | | | |
|---|---|---|---|
| 1032595 | 12/1956 | Fed. Rep. of Germany | 260/543 R |
| 1300796 | 12/1972 | United Kingdom | 260/455 A |

OTHER PUBLICATIONS

J. Chem. Res., (1977), pp. 2801–2809.
Acta Chem. Scand., 17, (1963), p. 2142.
Ann., 729, (1969), p. 44.
Angew. Chemie, 89, (1977), pp. 789–796.
Conant, The Chemistry of Organic Compounds, MacMillan Company, New York, 1939.
Atkins et al., J. Amer. Chem. Soc., 89, (1967), p. 2503.
Bartholomew et al., J. Chem. Research, 1977, pp. 2813–2825.

Primary Examiner—John M. Ford
Assistant Examiner—Robert C. Whittenbaugh
Attorney, Agent, or Firm—Keil & Witherspoon

[57] ABSTRACT

Sulfamic acid halides and processes for the preparation of sulfamic acid halides by reaction of monosubstituted sulfamic acid halides with halogen compounds in the presence of specific amounts of a basic compound and in the presence of an organic solvent, if desired with subsequent treatment with water at a pH of at most 7. The compounds obtainable by the process of the invention, some of which are new, are valuable starting materials for the preparation of crop protection agents, dyes and drugs.

8 Claims, No Drawings

SULFAMIC ACID HALIDES AND PROCESSES FOR THE PREPARATION OF SULFAMIC ACID HALIDES

The present invention relates to novel sulfamic acid halides and to processes for the preparation of sulfamic acid halides by reaction of monosubstituted sulfamic acid halides with halogen compounds in the presence of specific amounts of a basic compound and in the presence of an organic solvent, if desired with subsequent treatment with water at a pH of at most 7.

French Pat. No. 735,765 discloses the preparation of N-acylsulfamic acid chlorides by reaction of acylanilides with elementary sodium, and subsequent reaction with sulfuryl chloride. However, the process is difficult to reproduce, gives the end product in poor yield and, because it entails the handling of metallic sodium, is unsuitable for large-scale industrial operation. Further, German Laid-Open application DOS No. 1,943,234 has disclosed the reaction of N-alkylsulfamic acid fluorides with acyl halides to give the corresponding N-fluorosulfonyl compounds. It is true that this process gives a good yield of end product, but it is unsatisfactory as regards the preparation of the alkylsulfamic acid fluorides used, and the difficulty of handling hydrogen fluoride, which is corrosive and toxic. Thus, alkylsulfamic acid chlorides must first be converted, by treatment with hydrogen fluoride in a pressure apparatus for 6 hours at 80°–90° C., to the corresponding sulfamic acid fluorides, and distillation processes are needed to remove the excess hydrogen fluoride and to purify the sulfamic acid fluorides. For example, the yield achieved in the case of methylsulfamic acid fluoride is about 70 percent. The reaction of N-ethylsulfamic acid chloride itself with difluorochloromethanesulfenyl chloride to the corresponding sulfamic acid chloride compound has also been disclosed (German Laid-Open application DOS No. 1,953,356), but the product is only obtained in 48 percent yield. J. chem. Res. (M) 1977, 2,801–2,809 describes the reaction of sulfamic acid halides with phosgene in the presence of pyridine, with toluene as the solvent, to give N-alkyl-N-chlorosulfonylcarbamyl chlorides, but in this process the working up of the reaction mixture must be preceded by filtration through a Hyflo Supercell filter. The filtrate is then subjected to fractional distillation. If working up is carried out without the filtration process, no substantial amounts of pure end product are obtained. The reaction and working-up process are always carried out in the presence of organic solvents and in the absence of water. In a further stage, the carbamic acid chlorides can be converted to the corresponding carbamic acid esters by reaction with alcohols. At fairly high conversions, the filters block frequently and large amounts of Hyflo Supercell must be used. The process is unsuitable for economical large-scale industrial operation, for the reasons mentioned above and because the filter residue must be burnt or dumped.

German Laid-Open Application DOS No. 2,408,530 describes a process for the preparation of N-β-haloalkyl-N-alkylaminosulfonyl halides by reacting aziridines with sulfuryl halides. As the Examples show, the reaction is carried out in the absence of an added base and of water, and in the presence of an organic solvent. This process does not permit the synthesis of sulfamic acid chlorides which are substituted by halogen, acyl or hetero-atoms.

German Laid-Open Application DOS No. 2,634,485 describes a process for the preparation of sulfamic acid halides by reacting N-(α-haloalkyl)-sulfamic acid halides with alcohols. Advantageously, a base is used as the catalyst. The reaction, and working-up, are carried out in the absence of water and in the presence of an organic solvent. The process only permits the synthesis of alkoxymethyl-sulfamic acid halides, but these must not be substituted by N-acyl or hetero-atoms. The process is expensive and entails two steps.

All the above processes are unsatisfactory in respect of yield, easy availability of the starting materials, purity and range of the end products obtainable, simplicity and economy of operation, and non-pollution of the environment, particularly when operated on an industrial scale.

We have found that a sulfamic acid halide of the formula

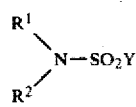

where $R^1$ is an aliphatic or cycloaliphatic radical, $R^2$ is

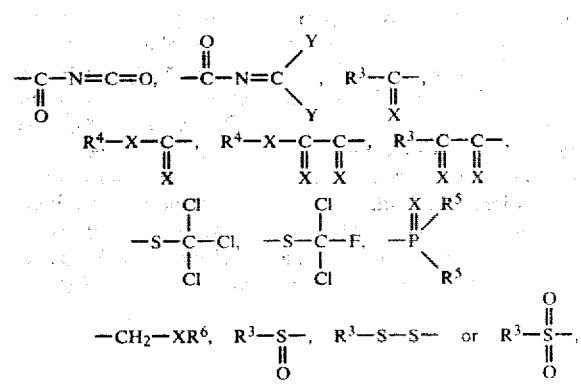

$R^3$ and $R^4$ are each an aliphatic, cycloaliphatic, araliphatic, aromatic or heterocyclic radical, $R^3$ may also be halogen, the individual radicals $R^5$ may be identical or different and each is halogen, $-X-R^6$ or $-R^6$, $R^6$ is an aliphatic radical, the individual radicals X may be identical or different and each is oxygen or sulfur, and the individual radicals Y are identical or different and each is halogen, may be obtained in an advantageous manner by reacting a sulfamic acid halide with a halogen compound in the presence of a base and a solvent, if a monosubstituted sulfamic acid halide of the formula

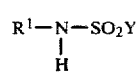

where $R^1$ and Y have the above meanings, is reacted with a halogen compound of the formula

where $R^2$ and Y have the above meanings, in the presence of from 1 to 1.5 equivalents of a basic compound per mole of starting material II, and of an inert, organic solvent, and, if desired, the resulting reaction mixture is subsequently treated with water at a pH of at most 7.

Further, we have found the novel sulfamic acid halides of the formula

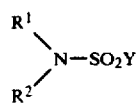

where $R^1$ is an aliphatic or cycloaliphatic radical, $R^2$ is

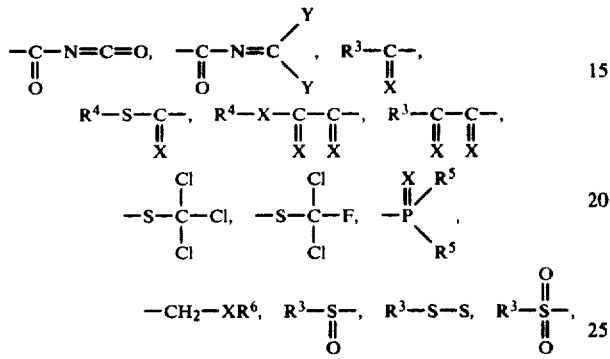

propoxycarbonyl or isopropoxycarbonyl, $R^3$ and $R^4$ are each an aliphatic, cycloaliphatic, araliphatic, aromatic or heterocyclic radical, $R^3$ may also be halogen, the individual radicals $R^5$ may be identical or different and each is halogen, $-X-R^6$ or $-R^6$, $R^6$ is an aliphatic radical, the individual radicals X may be identical or different and each is oxygen or sulfur, and the individual radicals Y are identical or different and each is halogen and, if $R^2$ is $-CH_2-X-R^6$, $R^1$ is an aliphatic or cycloaliphatic radical which is halogen-free in the β-position to the nitrogen, and X is sulfur, or, if $R^2$ is

$R^1$ is a cycloaliphatic radical, ethyl, n-propyl or an aliphatic radical of not less than 4 carbon atoms, or, if $R^2$ is

$R^1$ is a cycloalkyl radical, or, if $R^2$ is

$R^1$ is substituted alkyl or cycloalkyl, or, if $R^2$ is

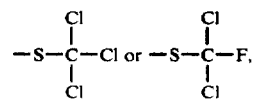

$R^1$ is a cycloaliphatic radical or an aliphatic radical which contains at least 5 carbon atoms and/or heteroatoms.

Where isopropylsulfamic acid chloride and methyl chloroformate are used, the reaction can be represented by the equation:

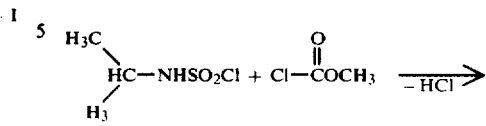

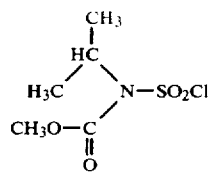

Where isopropylsulfamic acid chloride and chlorocarbonyl isocyanate are used, the reaction may be represented by the following equation:

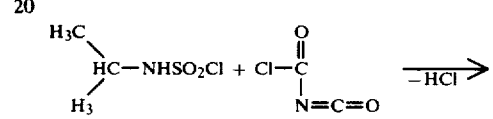

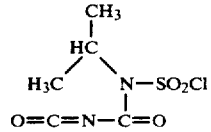

Compared to the prior art, the process according to the invention gives, more simply and more economically, a large number of novel and known N,N-disubstituted sulfamic acid halides in better yield and higher purity. The reaction time is short, and working up of the reaction mixture is simple and safe, particularly with a view to protection of the environment. Starting materials II with alkyl of relatively high carbon number as the substituents, and with or without halogen atoms as substituents, can be reacted in accordance with the process of the invention. Working up of the reaction mixture is simpler and safer, also from the point of view of protection of the environment. All these advantageous results are surprising in view of the prior art. It was not foreseeable, in view of German Laid-Open Application DOS No. 1,943,234, that the sulfamic acid chlorides could advantageously be reacted without prior conversion to the corresponding sulfamic acid fluorides. Because of the highly toxic nature of disubstituted sulfamic acid fluorides (compare Houben-Weyl, Methoden der Organischen Chemie, Volume 11/2, page 703), the process according to the invention is therefore particularly advantageous from the point of view of environmental pollution, and compared to the process of German Laid-Open Application DOS No. 1,953,356 it gives better yields. Surprisingly, it can also be carried out without using Hyflo Supercell filters. In the case of chlorocarbonylsulfamic acid chlorides, the process according to the invention gives the desired end products in higher yield and greater purity, and without polluting the environment.

An acid or neutral aqueous washing process is not necessary if $R^2$ is

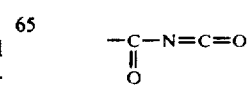

but may be of importance for the success of the reaction if $R^2$ is

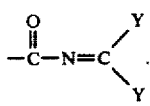

It is also surprising that it is possible to carry out an acid or neutral, aqueous washing process, which is of critical importance for the success of the reaction in all cases of starting materials where $R^2$ has one of its other meanings. If, for example, in the case of the reaction of an alkylsulfamic acid chloride with methyl chloroformate the after-treatment with water is omitted, the subsequent distillation gives, even under mild conditions, only a small amount of low-boiling decomposition products together with a viscous reaction residue, which is very largely not distillable. The feasibility of this washing process according to the invention was unforeseeable, since, though sulfamic acid fluorides are to some extent stable to water, sulfamic acid chlorides decompose extremely vigorously in the presence of water. A high degree of sensitivity to hydrolysis is described in Acta Chem. Scand., 17 (1963), 2,142 ("they react very rapidly with water") and Ann., 729 (1969), 44 ("they react vigorously and exothermically with water").

The starting materials III can be prepared in accordance with conventional processes, for example by reacting a cyanogen halide with a carbonic acid dihalide by the method described in Angew. Chemie, 89 (1977), 789–796.

The starting material II can be reacted with a stoichiometric amount or an excess of a starting material III, preferably using a ratio of from 1 to 1.5 moles, especially from 1 to 1.1 moles, of III per mole of II.

Preferred starting materials II and III and accordingly preferred end products I are those where $R^1$ is straight-chain or branched alkyl of 1 to 20, especially of 1 to 8, carbon atoms, which is unsubstituted or polysubstituted by halogen, especially fluorine and/or chlorine, or monosubstituted by halogen, especially fluorine or chlorine, advantageously in the β-, γ- and/or δ-position to the nitrogen, or is cycloalkyl of 4 to 8 carbon atoms, $R^2$ is

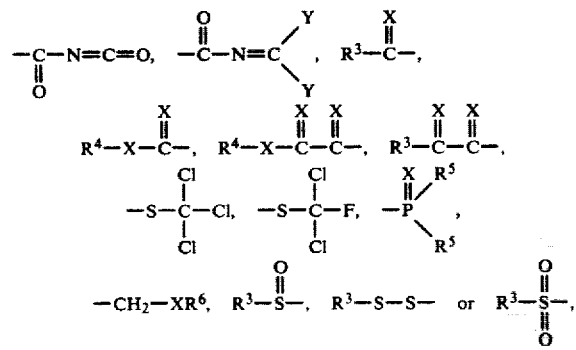

$R^3$ and $R^4$ are each alkyl of 1 to 20, preferably of 1 to 8, carbon atoms, which is unsubstituted or is substituted by one or two ether groups, advantageously of 1 to 4 carbon atoms in the alkoxy group, and/or by one or two halogen atoms, preferably fluorine or chlorine, (the stated number of carbon atoms of the alkyl radical being exclusive of the carbon atoms of the ether groups), or straight-chain or branched alkenyl or alkynyl of 2 to 20, especially of 2 to 8, carbon atoms, which is unsubstituted or is substituted by one or two ether groups, advantageously of 1 to 4 carbon atoms in the alkoxy group, and/or by one or two halogen atoms, preferably fluroine or chlorine (the stated number of carbon atoms of the alkenyl or alkynyl radical being exclusive of the carbon atoms of the ether groups), or cycloalkyl of 4 to 8 carbon atoms which is unsubstituted or substituted by a chlorine atom, or aralkyl or alkylaryl of 7 to 12 carbon atoms which is unsubstituted or substituted by 1 or 2 halogen atoms, nitro groups and/or alkoxy groups of 1 to 3 carbon atoms (the stated number of carbon atoms of the aralkyl or alkylaryl radical being exclusive of the carbon atoms of the ether groups), or aryl of 6 to 12 carbon atoms which is unsubstituted or is substituted by one or 2 halogen atoms, nitro groups and/or alkoxy groups of 1 to 3 carbon atoms (the stated number of carbon atoms of the aryl radical being exclusive of the carbon atoms of the ether groups) or a 5-membered or 6-membered heterocyclic radical, which can contain one or two nitrogen atoms and/or an oxygen atom and is unsubstituted or is substituted by 1 or 2 halogen atoms, nitro groups and/or alkoxy groups of 1 to 3 carbon atoms, $R^3$ may also be fluorine or especially chlorine, the individual radicals $R^5$ may be identical or different and each is chlorine, $-X-R^6$ or $-R^6$, $R^6$ is alkyl of 1 to 20, especially 1 to 8, preferably 1 to 3, carbon atoms, the individual radicals X may be identical or different and each is oxygen or sulfur and the individual radicals Y may be identical or different and each is bromine, fluorine or especially chlorine.

The stated radicals may in addition be substituted by groups which are inert under the reaction conditions, for example alkyl of 1 to 4 carbon atoms, carbalkoxy of 2 to 4 carbon atoms or chlorocarbonyl.

Preferred starting materials II are methylsulfamic acid chloride, ethylsulfamic acid chloride, n-propylsulfamic acid chloride, isopropylsulfamic acid chloride, n-butylsulfamic acid chloride, sec.-butylsulfamic acid chloride, isobutylsulfamic acid chloride, tert.-butylsulfamic acid chloride, pentylsulfamic acid chloride, cyclopentylsulfamic acid chloride, n-hexylsulfamic acid chloride, cyclohexylsulfamic acid chloride, n-heptylsulfamic acid chloride, 1,2-dimethylbutyl-1-sulfamic acid chloride, 1,3-dimethylbutyl-1-sulfamic acid chloride, 3-chloropentyl-1-sulfamic acid chloride, 3-chloropropyl-1-sulfamic acid chloride, 4-chloroisoamyl-1-sulfamic acid chloride, 2-chloromethylpropyl-1-sulfamic acid chloride, 2-fluoromethylpropyl-1-sulfamic acid chloride, 1-chloropropyl-2-sulfamic acid chloride, 2-chloropropyl-1-sulfamic acid chloride, 2-chloroisobutyl-1-sulfamic acid chloride, 1-chlorobutyl-2-sulfamic acid chloride, 3-chlorobutyl-2-sulfamic acid chloride, 2-fluoroethyl-1-sulfamic acid chloride, 1-fluoropropyl-2-sulfamic acid chloride, 2-fluoropropyl-1-sulfamic acid chloride, 1-fluorobutyl-2-sulfamic acid chloride, 2-fluorobutyl-1-sulfamic acid chloride, 2-fluoroisobutyl-1-sulfamic acid chloride, 3-fluorobutyl-1-sulfamic acid chloride, 4-chloropentyl-1-sulfamic acid chloride, 4-chlorobutyl-2-sulfamic acid chloride and chloro-tert.-butylsulfamic acid chloride, and corresponding sulfamic acid fluorides, eg. methylsulfamic acid fluoride, ethylsulfamic acid fluoride, n-propylsulfamic acid fluoride, isopropylsulfamic acid fluoride, n-butylsulfamic acid fluoride, isobutylsulfamic acid fluoride, tert.-butylsulfamic acid fluoride, sec.-butylsulfamic acid fluoride, pentylsulfamic acid fluoride, cyclopentylsulfamic acid fluoride, n-hexylsulfamic acid fluoride, cyclohexylsulfamic acid fluoride, n-heptylsulfamic acid fluoride, 1,2-dimethylbutyl-1-sulfamic acid fluoride and 1,3-dimethylbutyl-1-sulfamic acid fluoride.

Advantageous starting materials III are acetyl chloride, propionyl chloride, butyryl chloride, valeryl chloride, isovaleryl chloride, sec.-valeryl chloride, caproyl chloride, α-methylvaleryl chloride, caprylyl chloride, enanthyl chloride, pelargonyl chloride, capryl chloride, undecanoyl chloride, dodecanoyl chloride, tridecanoyl chloride, tetradecanoyl chloride, pentadecanoyl chloride, hexadecanoyl chloride, acetoxyacetyl chloride, chloroacetyl chloride, dichloroacetyl chloride, α-chloropropionyl chloride, α,α-dichloropropionyl chloride and α-chlorobutyryl chloride; analogous carboxylic acid fluorides; α-chlorovaleryl chloride, α-chlorocaproyl chloride, β-chloropropionyl chloride, pyridine-2-carboxylic acid chloride, pyrrole-2-carboxylic acid chloride, piperidine-2-carboxylic acid chloride, piperazine-2-carboxylic acid chloride, furan-2-carboxylic acid chloride, fluoroacetyl chloride, acryloyl chloride, but-2-en-1-oyl chloride, pent-3-en-1-oyl chloride, β-methoxypropionyl chloride, γ-methoxybutyryl chloride, cyclopentanoyl chloride, cyclohexanoyl chloride, benzoyl chloride, α-naphthoyl chloride, o-, m- and p-chlorobenzoyl chloride, o-, m- and p-nitrobenzoyl chloride, phosgene, chlorocarbonyl fluoride, difluorophosgene, thiophosgene, oxalyl chloride and phenylacetyl chloride; analogous thiocarboxylic acid chlorides; methoxymethyl chloride, ethoxymethyl chloride and methylthiomethyl chloride; methyl chloroformate, ethyl chloroformate, ispropyl chloroformate, n-propyl chloroformate, butyl chloroformate, isobutyl chloroformate, sec.-butyl chloroformate and phenyl chloroformate; monoalkyl oxalate monochlorides analogous to the above compounds; analogous thioesters; analogous dithioesters; disulfur dichloride, thionyl chloride, thionyl fluoride, sulfuryl chloride, sulfuryl fluoride, methylsulfonyl chloride, ethylsulfonyl chloride, n-propylsulfonyl chloride, isopropylsulfonyl chloride, n-butylsulfonyl chloride, sec.-butylsulfonyl chloride, benzenesulfonyl chloride, o-, m- and p-toluenesulfonyl chloride, o-, m- and p-chlorobenzenesulfonyl chloride, o-, m- and p-nitrobenzenesulfonyl chloride and β-naphthalenesulfonyl chloride; analogous sulfonyl fluorides; trichloromethyl-sulfur chloride and monofluorodichloromethyl-sulfur chloride; O,O-dimethylphosphoric acid chloride, O,O-diethylphosphoric acid chloride, O-methyl-O-ethylphosphoric acid chloride, O,S-dimethylmonothiophosphoryl chloride, O-ethyl-S-n-propyl-monothiophosphoryl chloride, phosphorus oxychloride, thiophosphoryl chloride, dimethylphosphinic acid chloride, diethylphosphinic acid chloride, ethylphosphinic acid dichloride, O-methylphosphoric acid dichloride, chlorocarbonyl isocyanate, N-chlorocarbonylisocyanide dichloride and N-fluorocarbonylisocyanide dichloride.

The reaction is as a rule carried out at from −50 to +80° C. In the case of starting materials III, where R² is

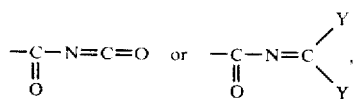

it is expediently carried out at from −50° to +70° C., advantageously from −30° to +60° C., preferably from −10° to +40° C., especially from 0° to 30° C.; in the case of all other starting materials III it is preferably carried out at from −10° to +40° C., especially from 0° to 30° C. The reaction is carried out under atmospheric or superatmospheric pressure, continuously or batchwise. Advantageously, an organic solvent which is inert under the reaction conditions is used. Examples of suitable solvents are halohydrocarbons, especially chlorohydrocarbons, eg. tetrachloroethylene, 1,1,2,2- or 1,1,1,2-tetrachloroethane, amyl chloride, cyclhexyl chloride, dichloropropane, methylene chloride, dichlorobutane, isopropyl bromide, n-propyl bromide, butyl bromide, chloroform, ethyl iodide, propyl iodide, chloronaphthalene, dichloronaphthalene, carbon tetrachloride, 1,1,1- and 1,1,2-trichloroethane, trichloroethylene, pentachloroethane, o-, m- and p-difluorobenzene, 1,2-dichloroethane, 1,1-dichloroethane, n-propyl chloride, 1,2-cis-dichloroethylene, n-butyl chloride, 2-, 3-and iso-butyl chloride, chlorobenzene, fluorobenzene, bromobenzene, iodobenzene, o-, p- and m-dichlorobenzene, o-, p-and m-dibromobenzene, o-, m- and p-chlorotoluene, 1,2,4-trichlorobenzene, 1,10-dibromodecane and 1,4-dibromobutane; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and β,β'-dichlorodiethyl ether; nitrohydrocarbons, eg. nitromethane, nitroethane, nitrobenzene, o-, m- and p-chloronitrobenzene and o-nitrotoluene; nitriles, eg. acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions with boiling ranges of from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; aromatic hydrocarbons, eg. benzene, toluene, o-, m- and p-xylene, tetralin, and 1,3,5-trimethylbenzene; and appropriate mixtures. Advantageously, the solvent is used in an amount of from 100 to 2,000 percent by weight, preferably from 400 to 800 percent by weight, based on starting material II.

The reaction is carried out in the presence of from 1 to 1.5, preferably from 1 to 1.2, equivalents of a basic compound per mole of starting material II. Preferred basic compounds are alkali metal compounds, alkaline earth metal compounds, ammonium compounds and, in particular, tertiary amines, as well as mixtures of these. However, zinc compounds can also be used. Specific examples of basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, sodium propionate, sodium butyrate, sodium isobutyrate, potassium formate, potassium acetate, potassium propionate, potassium butyrate, potassium isobutyrate, potassium tert.-butyrate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidone, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, α-picoline, β-picoline, γ-picoline, isoquinoline, pyrimidine, acridine, N,N,N',N'-tetramethylethylenediamine, N,N,N',N'-tetraethylethylenediamine, quinoxaline, qhinazoline, N-propyldiisopropylamine, N,N-dimethylcyclohexylamine, 2,6-lutidine, 2,4-lutidine, trifurfurylamine and triethylenediamine.

The reaction is carried out as follows: a mixture of starting materials II and III, basic compound and organic solvent is kept at the reaction temperature for from 0.1 to 6 hours, in the case of starting materials III, where $R^2$ is

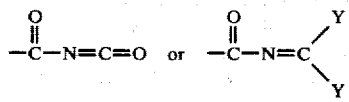

advantageously for from 0.3 to 6 hours, preferably from 0.5 to 3 hours, and in all other cases for from 0.1 to 5 hours, preferably from 0.2 to 1 hour. For example, it is possible to mix the starting material II, the starting material III and the solvent, and then to add the basic compound and keep the mixture at the reaction temperature. In a preferred embodiment of the process according to the invention, the starting material III is mixed with the basic compound for from 10 to 30 minutes in an inert organic solvent at from −50° to +40° C., preferably from −10° to +30° C., and the starting material II is then added at the same temperature in the course of from 10 to 30 minutes. To complete the reaction, stirring is then continued for from 0.1 to 4 hours at from 0° to 40° C., especially for from 0.2 to 0.3 hour at from 10° to 30° C.

In the case of starting materials III, where $R^2$ is

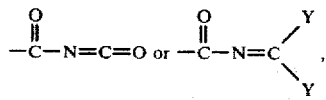

in a preferred embodiment of the process according to the invention, the starting material III is mixed with the basic compound for from 10 to 30 minutes in an inert organic solvent at from −50° to +40° C., preferably from −20° to +30° C., and the starting material II is then added at the same temperature in the course of from 10 to 30 minutes. To complete the reaction, stirring is then continued for from 0.1 to 5 hours at from 0° to 45° C., especially for from 0.2 to 2 hours at from 10° to 30° C.

If necessary, the reaction mixture obtained can be filtered and the filter residue washed with one of the above solvents, for example methylene chloride or toluene. In the case of starting materials III, where $R^2$ is

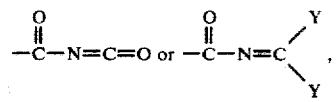

the end product is then isolated in the conventional manner, for example by separating off the organic phase and subjecting it to fractional distillation.

Optionally, if $R^2$ is

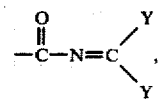

and advantageously if $R^2$ has other meanings, a subsequent treatment with water can be carried out, preferably immediately after completion of the reaction. Advantageously, the reaction mixture or the above filtrate is treated with water for from 2 to 30 minutes at from 0° to 30° C., especially from 5° to 15° C., at a pH of from 1 to 7, preferably from 1 to 5, especially from 1 to 3, under atmospheric or superatmospheric pressure, continuously or batchwise. The water treatment acts like an extraction and 2 phases form. The end product is then isolated in the conventional manner, for example by separating off the organic phase and subjecting it to fractional distillation.

However, after a treatment with water the crude end product obtained is in many cases already sufficiently pure that, after stripping off the solvent, it can be employed directly for further reactions.

The compounds obtainable by the process of the invention, some of which are new, are valuable starting materials for the preparation of crop protection agents, dyes and drugs. For example, reaction of N-acetyl-N-methyl-aminosulfamic acid chloride with 2,3-dihydro-3,3-dimethyl-2-ethoxy-benzofuran in ether in the presence of an equivalent amount of triethylamine smoothly and directly gives 2,3-dihydro-3,3-dimethyl-2-ethoxybenzofuran-5-yl-N-methyl-carbonyl-N-methyl-aminosulfonate ($n_D^{25}=1.5042$), which hitherto had only been prepared by first producing the methylaminosulfamic acid ester and then acetylating it (German Laid-Open Application DOS No. 2,402,370); this compound is an excellent herbicide. Similarly, reaction with N-alkylsulfonyl-N-alkyl-sulfamic acid chlorides or N-alkoxycarbonyl-N-alkylsulfamic acid chlorides gives nitrogen-substituted 2,3-dihydro-3,3-dimethyl-2-alkoxybenzofuran-5-yl-aminosulfonates, the excellent herbicidal action of which is described in German Laid-Open Application DOS No. 2,402,370. Further possible uses are mentioned in Example 32.

For example, reaction of N-carbonylisocyanato-N-alkyl-(cycloalkyl)-sulfamic acid chlorides with alkylamines, for example isopropylamine, gives N-alkyl-N'-(N''-methyl-N''-chlorosulfonyl)-carbamidoureas; these compounds have an excellent herbicidal action. Analogously, reaction of N-carbonylisocyanato-N-alkyl-(N-cycloalkyl)-sulfamic acid chlorides with substituted anilines gives biurets correspondingly substituted at both terminal nitrogens, and these compounds can be converted by strongly alkaline hydrolysis to the herbicidal biurets described in German Published Application DAS No. 1,032,595. Similarly, N-carbonylisocyanide-dichlorido-N-alkyl-(N-cycloalkyl)-sulfamic acid chlorides can, after conversion to the above N-carbonylisocyanato compounds I by means of acid aqueous hydrolysis, be converted to the above biurets. Further possible uses are mentioned in Example 44.

In the Examples which follow, parts are by weight.

EXAMPLE 1

(a) 21.3 parts of triethylamine in 40 parts of toluene are introduced, at 10° C., into a solution of 36.5 parts of dichlorofluoromethylsulfenyl chloride in 90 parts of toluene. 30.2 parts of ethylsulfamic acid chloride are then added at 18° C. in the course of 10 minutes, and the reaction mixture is stirred for half an hour at 22° C. Thereafter, the mixture is stirred for 5 minutes with 300 parts of water at 10° C. and pH 1. The organic phase is then separated off from the 2-phase mixture formed, and is filtered and subjected to fractional distillation. 38.1 parts (68.9% of theory) of N-dichlorofluoromethylthio-N-ethylsulfamic acid chloride, of boiling point 65°–76° C./0.08 mbar and $n_D^{25} = 1.4976$, are obtained.

(b) (Comparison):

The reaction is carried out similarly to Example (1a), but without the treatment with water. After completion of the reaction, the mixture is filtered, the filter residue is washed with toluene and the filtrate is concentrated and distilled. 11.9 parts (21.6% of theory) of end product I, of boiling point 81°–105° C./0.13 mbar and $n_D^{25} = 1.5020$, are obtained.

(c) (Comparison):

The reaction is carried out similarly to Example (1b), but the base is added to the mixture of the two starting materials. 5.17 parts (9.4% of theory) of end product I, of boiling point 71°–101° C./0.13 mbar and $n_D^{25} = 1.5009$, are obtained.

EXAMPLE 2

(a) 39.6 parts of pyridine are added in the course of 15 minutes at 10° C., whilst stirring, to a mixture of 47.2 parts of methyl chloroformate and 78.8 parts of isopropylsulfamic acid chloride in 330 parts of methylene chloride. The reaction mixture is then stirred for 10 minutes at 22° C. Thereafter, the mixture is stirred for 8 minutes with 350 parts of water at 6° C. and pH 1. The organic phase is then separated off from the 2-phase mixture formed, and is filtered and subjected to fractional distillation. 72.1 parts (67% of theory) of N-methoxycarbonyl-N-isopropylsulfamic acid chloride, of boiling point 60°–64° C./0.13 mbar and $n_D^{25} = 1.4540$, are obtained.

(b) (Comparison):

The reaction is carried out similarly to Example (2a), but, as in Example (1b), without treatment with water. 14.5 parts (13.5% of theory) of heavily contaminated end product I, of boiling point 60°–80° C./0.13 mbar and $n_D^{25} = 1.4912$, are obtained.

(c) (Comparison):

The reaction is carried out similarly to Example (2a), but without treatment with water. The reaction mixture is stirred for 10 minutes at room temperature. After filtering, washing the filter residue with methylene chloride and filtering the methylene chloride filtrate through a Hyflo Supercell filter, the combined filtrate is concentrated under reduced pressure. 16.1 parts (15% of theory) of heavily contaminated end product I, of boiling point 72°–83° C./0.13 mbar and $n_D^{25} = 1.5022$, are obtained.

EXAMPLE 3

158.2 parts of pyridine are added at $-10°$ C., while stirring, to a solution of 188.8 parts of methyl chloroformate in 1,200 parts of methylene chloride. Then 259.2 parts of methylsulfamic acid chloride are added at the same temperature while stirring, and the mixture is stirred for half an hour at 0° C. and for one hour at 25° C. The reaction mixture is then stirred for 6 minutes with 600 parts of water at 5° C. and pH 1. The organic phase is then separated off from the 2-phase mixture formed, and is filtered and subjected to fractional distillation. 341 parts (91% of theory) of N-methoxycarbonyl-N-methylsulfamic acid chloride, of boiling point 49°–51° C./0.13 mbar and $n_D^{25} = 1.4600$, are obtained.

EXAMPLES 4 to 7

The reaction is carried out similarly to Example 3 and the following compounds are obtained

TABLE 1

| Example | Parts of starting material III $Cl-\overset{O}{\underset{\|}{C}}-OCH_3$ | Parts of starting material II RNHSO₂Cl | R | Parts of pyridine | Parts of end product I CH₃O | O | Boiling point (°C.)/mbar | $n_D^{25}$ | Yield (% of theory) |
|---|---|---|---|---|---|---|---|---|---|
| 4 | 330.4 | 502.6 | C₂H₅ | 277.2 | 634 | | 50–60/0.1 | 1.4575 | 90 |
| 5 | 189.0 | 315.2 | nC₃H₇ | 158.2 | 354 | | 120/0.13ᵃ | 1.4628 | 82 |
| 6 | 47.2 | 89.0 | Cl—CH₂—CH₂ | 39.6 | 101.5 | | 84–88/0.11 | 1.4851 | 86 |
| 7 | 24.8 | 50.5 | ⟨H⟩ | 20.7 | 33.1 | | 91/0.12 | 1.4845 | 50 |

ᵃThin film evaporator

EXAMPLE 8

316.4 parts of pyridine are introduced at $-10°$ C., whilst stirring, into a solution of 400 parts of phosgene in 2,500 parts of 1,2-dichloroethane. 630.4 parts of isopropylsulfamic acid chloride are then added at the same temperature and the reaction mixture is stirred for one hour at 22° C. Thereafter, the mixture is stirred for 8 minutes with 700 parts of water at 6° C. and pH 1. The organic phase is then separated off from the 2-phase mixture formed, and is filtered and subjected to fractional distillation. 763 parts (87% of theory) of N-chlorocarbonyl-N-isopropylsulfamic acid chloride, of boiling point 57°–62° C./0.11 mbar and $n_D^{25} = 1.4749$, are obtained.

EXAMPLES 9 to 12

The following compounds are obtained similarly to Example 8:

TABLE 2

| Ex- ample | Parts of starting material III $Cl-\overset{O}{\underset{\|}{C}}-Cl$ | Parts of starting material II RNHSO$_2$Cl | R | Parts of base | Parts of end product I $\underset{Cl-\overset{\|}{\underset{O}{C}}}{\overset{R}{\diagdown}}N-SO_2Cl$ | Boiling point (°C.)/mbar | $n_D^{25}$ | Yield (% of theory) |
|---|---|---|---|---|---|---|---|---|
| 9 | 328 | 368 | CH$_3$ | 224.6 pyridine | 447.2 | 49–51/0.11 | 1.4861 | 82 |
| 10 | 345 | 430.7 | C$_2$H$_5$ | 237 pyridine | 525.4 | 57/0.12 | 1.4798 | 85 |
| 11 | 205 | 315.2 | nC$_3$H$_7$ | 186.2 α-picoline | 343.3 | 67–72/0.12 | 1.4770 | 78 |
| 12 | 345 | 514.8 | nC$_4$H$_9$ | 382 N,N-dimethyl-cyclohexylamine | 480 | 70–76/0.12 | 1.4769 | 68.4 |

EXAMPLE 13

197.8 parts of pyridine are introduced in the course of 20 minutes at −10° C., whilst stirring, into a solution of 196.3 parts of acetyl chloride in 1,350 parts of methylene chloride. 359 parts of ethylsulfamic acid chloride are then added at the same temperature. The reaction mixture is stirred for half an hour at 0° C. and one hour at 22° C. Thereafter, the mixture is stirred for 5 minutes with 800 parts of water at 9° C. and pH 1. The organic phase is then separated off from the 2-phase mixture formed, and is filtered and subjected to fractional distillation. 367 parts (79% of theory) of N-acetyl-N-ethylsulfamic acid chloride, of boiling point 34°–40° C./0.11 mbar and $n_D^{25} = 1.4595$, are obtained.

EXAMPLES 14 to 19

The following compounds are obtained in the same way as in Example 13:

TABLE 3

| Ex. | Parts of Starting material III | Parts of Starting material II | Parts of pyridine | Parts of End product I | b.p. (°C.)/mbar | $n_D^{25}$ | Yield (% of theory) |
|---|---|---|---|---|---|---|---|
| 14 | 39.3  CH$_3$–$\overset{O}{\underset{\|}{C}}$–Cl | 64.8 CH$_3$NHSO$_2$Cl | 39.6 | 72.2  $\underset{CH_3-\overset{\|}{\underset{O}{C}}}{\overset{CH_3}{\diagdown}}N-SO_2Cl$ | 75/17 | 1.4668 | 84 |
| 15 | 39.3  CH$_3$–$\overset{O}{\underset{\|}{C}}$–Cl | 78.8 nC$_3$H$_7$NHSO$_2$Cl | 39.6 | 80.8  $\underset{CH_3\overset{\|}{\underset{O}{C}}}{\overset{nC_3H_7}{\diagdown}}N-SO_2Cl$ | 45/0.11 | 1.4610 | 81 |
| 16 | 39.3  CH$_3$–$\overset{O}{\underset{\|}{C}}$–Cl | 78.8 iC$_3$H$_7$NHSO$_2$Cl | 39.6 | 78.6  $\underset{CH_3\overset{\|}{\underset{O}{C}}}{\overset{iC_3H_7}{\diagdown}}N-SO_2Cl$ | 75–83/8.4 | 1.4608 | 79 |
| 17 | 39.3  CH$_3$–$\overset{O}{\underset{\|}{C}}$–Cl | 85.8 nC$_4$H$_9$NHSO$_2$Cl | 39.6 | 81.1  $\underset{CH_3\overset{\|}{\underset{O}{C}}}{\overset{nC_4H_9}{\diagdown}}N-SO_2Cl$ | 59–62/0.11 | 1.4616 | 76 |
| 18 | 39.3  CH$_3$–$\overset{O}{\underset{\|}{C}}$–Cl | 89.0 Cl–CH$_2$–CH$_2$NHSO$_2$Cl | 39.6 | 85.8  $\underset{CH_3\overset{\|}{\underset{O}{C}}}{\overset{ClCH_2-CH_2}{\diagdown}}N-SO_2Cl$ | 73–75/0.11 | 1.4922 | 78 |
| 19 | 98.4  C$_6$H$_5$CCl ($\overset{O}{\|}$) | 100 C$_2$H$_5$NHSO$_2$Cl | 55.4 | 114  $\underset{\underset{C_6H_5}{\diagup}\overset{\|}{\underset{O}{C}}\diagdown}{\overset{C_2H_5}{\diagdown}}N-SO_2Cl$ | 87–103/0.11 | 1.5368 | 69 |

EXAMPLE 20

79.1 parts of pyridine are added at 15° C., whilst stirring, to a solution of 139.5 parts of oxalic acid dichloride in 500 parts of toluene. 157.6 parts of isopropylsulfamic acid chloride are then added whilst cooling with ice, after which the mixture is stirred for one hour at 22°

C. Thereafter, the mixture is stirred for 5 minutes with 200 parts of water at 8° C. and pH 1. The organic phase is then separated off from the 2-phase mixture formed, and is filtered and subjected to fractional distillation. 151 parts (61% of theory) of N-chlorooxalyl-N-isopropylsulfamic acid chloride, of boiling point 70°–72° C./2 mbar and $n_D^{25} = 1.4723$, are obtained.

EXAMPLES 21 to 29

The following compounds are obtained similarly to Example 20:

methylsulfamic acid chloride are then added at the same temperature in the course of 20 minutes, after which stirring is continued for 45 minutes at 22° C. Thereafter, the mixture is stirred for 5 minutes with 150 parts of water at 11° C. and pH 1. The organic phase is then separated off from the two-phase mixture formed, and is filtered and subjected to distillation. 97.4 parts (89.5% of theory) of N-ethylmercaptocarbonyl-N-methylsulfamic acid chloride, of boiling point 75°–78° C./0.12 mbar and $n_D^{25} = 1.5078$, are obtained.

TABLE 4

| Ex. | Parts of | starting material III | Parts of | starting material II | Parts of pyridine | Parts of | End product I | b.p. (°C.)/mbar | $n_D^{25}$ | Yield (% of theory) |
|---|---|---|---|---|---|---|---|---|---|---|
| 21 | 27.9 | ClC(O)—C(O)Cl | 25.9 | CH$_3$NHSO$_2$Cl | 15.8 | 26 | H$_3$C\N—SO$_2$Cl / Cl—C(O)—C(O) | 60–65/2 | 1.4834 | 58 |
| 22 | 27.9 | ClC(O)—C(O)Cl | 28.7 | C$_2$H$_5$NHSO$_2$Cl | 15.8 | 20 | C$_2$H$_5$\N—SO$_2$Cl / Cl—C(O)—C(O) | 70–72/0.4 | 1.4790 | 42 |
| 23 | 139.5 | ClC(O)—C(O)Cl | 157.6 | (n)C$_3$H$_7$NHSO$_2$Cl | 79.1 | 107 | (n)C$_3$H$_7$\N—SO$_2$Cl / Cl—C(O)—C(O) | 75–84/0.66 | 1.4745 | 43 |
| 24 | 139.5 | ClC(O)—C(O)Cl | 171.6 | (n)C$_4$H$_9$NHSO$_2$Cl | 79.1 | 142 | (n)C$_4$H$_9$\N—SO$_2$Cl / Cl—C(O)—C(O) | 87–94/0.66 | 1.4720 | 54 |
| 25 | 30 | ClC(O)—COC$_2$H$_5$ | 25.9 | CH$_3$NHSO$_2$Cl | 15.8 | 26 | CH$_3$\N—SO$_2$Cl / H$_5$C$_2$O—C(O)—C(O) | 80–82/0.66 | 1.4587 | 61 |
| 26 | 30 | ClC(O)—COC$_2$H$_5$ | 28.7 | H$_5$C$_2$NHSO$_2$Cl | 15.8 | 34 | H$_5$C$_2$\N—SO$_2$Cl / H$_5$C$_2$O—C(O)—C(O) | 75–83/0.52 | 1.4579 | 70 |
| 27 | 30 | ClC(O)—COC$_2$H$_5$ | 31.5 | (n)C$_3$H$_7$NHSO$_2$Cl | 15.8 | 30.8 | (n)C$_3$H$_7$\N—SO$_2$Cl / H$_5$C$_2$O—C(O)—C(O) | 82–85/0.52 | 1.4573 | 60 |
| 28 | 150.1 | ClC(O)—COC$_2$H$_5$ | 157.6 | (i)C$_3$H$_7$NHSO$_2$Cl | 79.1 | 193 | (i)C$_3$H$_7$\N—SO$_2$Cl / H$_5$C$_2$O—C(O)—C(O) | 78–82/0.52 | 1.4539 | 75 |
| 29 | 30 | ClC(O)—C(O)—OC$_2$H$_5$ | 34.3 | (n)C$_4$H$_9$NHSO$_2$Cl | 15.8 | 36 | (n)C$_4$H$_9$\N—SO$_2$Cl / H$_5$C$_2$O—C(O)—C(O) | 100–110/0.66 | 1.4588 | 70 |

EXAMPLE 30

39.6 parts of pyridine are added at −10° C., whilst stirring, to a solution of 62.3 parts of thioethyl chloroformate in 300 parts of 1,2-dichloroethane. 64.8 parts of

EXAMPLE 31

Similarly to Example 30, employing 39.6 parts of pyridine, 69.3 parts of thio-n-propyl chloroformate and 85.5 parts of n-butylsulfamic acid chloride gives, after distillation on a thin film evaporator (140° C./0.12 mbar), 101 parts (73.8% of theory) of N-n-propylmercaptocarbonyl-N-n-butylsulfamic acid chloride of $n_D^{25} = 1.5000$.

EXAMPLE 32 (Use Example)

(a) 26.3 parts of N-methoxycarbonyl-N-methylsulfamic acid chloride from Example 3 and 18.2 parts of triethylamine are added uniformly from two dropping funnels, at 22° C., to a solution of 41.5 parts of 3,5-dibromo-4-hydroxybenzonitrile in 1,000 parts of acetonitrile, whilst stirring. The reaction mixture is then stirred for one hour at 60° C. and is concentrated under reduced pressure, and the residue is taken up in 400 parts of methylene chloride. After extraction with 200 parts by volume of 2 N sodium hydroxide solution, drying the organic phase over magnesium sulfate, chromatography over neutral aluminum oxide and concentration under reduced pressure, 2,6-dibromo-4-cyanophenyl-1-N-methoxycarbonyl-N-methylaminosulfonate, of melting point 93°–96° C., is obtained.

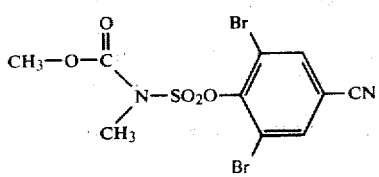

(b) The herbicidal activity of the end product of Example (32a) is ascertained in greenhouse experiments.

The containers used are plastic flowerpots of 300 cm³ capacity, filled with loamy sand containing about 1.5% of humus. The seeds of the test plants, segregated according to species, are sown shallow. In the case of the pre-emergence treatment, the active ingredient is applied to the soil surface immediately thereafter, by suspending or emulsifying it in water as the dispersing medium and spraying the suspension or emulsion onto the soil by means of atomizing nozzles. The amount applied is in each case 3.0 kg of active ingredient/ha. After application of the active ingredient, the pots are lightly sprinkled so as to stimulate germination and growth of the plants and at the same time to activate the chemical agents. The pots are then covered with transparent plastic covers until the plants have taken root. This cover ensures uniform germination of the test plants.

For post-emergence treatment, the plants are first grown in the test pots to a height of from 3 to 10 cm, depending on their growth habit, and are then treated. Here again the dose is 3 kg of active ingredient/ha. The pots are not covered. The experiments are carried out in a greenhouse, using the warmer parts of the greenhouse (25°–40° C.) for heat-loving species and using 15°–30° C. for temperate-zone plants. The test period is 4–6 weeks.

During this time, the plants are tended and their reaction to the individual treatments is evaluated on a scale from 0 to 100, 0 denoting no damage or normal germination and 100 denoting no germination of the plants or complete destruction of at least the visible parts of the shoots.

In the case of Sinapis alba, employed as an indicator plant, the pre-emergence effect is total; Ipomoea spp. and Centaurea cyanus are destroyed by the post-emergence treatment. The crop plants oats (Avena sativa) and Italian ryegrass (Lolium multiflorum) remain undamaged by both types of treatment. Compared to conventional compounds hitherto used for this purpose, these results show a substantially better effect in combating undesired broad-leaved plants in crops of gramineae.

EXAMPLE 33

7.9 parts of pyridine are introduced at $-10°$ C. into a solution of 11.6 parts of chlorocarbonyl isocyanate in 200 parts of toluene. 15.8 parts of isopropylsulfamic acid chloride are then added in the course of 15 minutes at $-10°$ C., and the reaction mixture is stirred for 2 hours at 22° C. After completion of the reaction, the mixture is filtered, the filter residue is washed with toluene, and the filtrate is concentrated and distilled. 16 parts (71% of theory) of N-isopropyl-N-carbonylisocyanatosulfamic acid chloride of boiling point 70°–72° C./0.3 mbar and $n_D^{25} = 1.4796$, are obtained.

EXAMPLES 34 to 38

The following compounds are obtained similarly to Example 33:

TABLE 5

| Example | Parts of starting material III $Cl-\overset{O}{\underset{\|}{C}}-N=C=O$ | Parts of starting material II $R^1NHSO_2Y$ | $R^1$ | Y | Parts of pyridine | Parts of end product I $R\diagdown N\diagup SO_2Y$ $O=\overset{\|}{C}-N=C=O$ | b.p. (°C./mbar) | $n_D^{25}$ | Yield (% of theory) |
|---|---|---|---|---|---|---|---|---|---|
| 34 | 5.8 | 6.47 | CH₃ | Cl | 3.95 | 7 | 56–60/0.2 | 1.4889 | 71 |
| 35 | 23.2 | 22.6 | CH₃ | F | 15.8 | 20 | 39–42/0.2 | 1.4361 | 55 |
| 36 | 5.8 | 7.17 | C₂H₅ | Cl | 3.95 | 7 | 68–70/0.3 | 1.4809 | 66 |
| 37 | 5.8 | 7.88 | n-C₃H₇ | Cl | 3.95 | 8 | 66–70/0.3 | 1.4808 | 71 |
| 38 | 5.8 | 8.57 | n-C₄H₉ | Cl | 3.95 | 8 | 70–75/0.3 | 1.4779 | 67 |

EXAMPLE 39

55.4 parts of pyridine are added at $-5°$ C., whilst stirring, to a mixture of 112.4 parts of chlorocarbonylisocyanide dichloride in 700 parts of 1,2-dichloroethane. 110.3 parts of n-propylamido-sulfamic acid chloride are then added at 0° C. in the course of 15 minutes. After stirring for 1½ hours at 22° C., the reaction mixture is filtered and the filtrate is stirred for 5 minutes with 300 parts of water at 5° C. and pH 1. The organic phase is then separated off from the 2-phase mixture formed, and is filtered and subjected to fractional distillation. 124.7 parts (63% of theory) of N-propyl-N-carbonylisocyanide-dichlorido-sulfamic acid chloride, of boiling point 95°–98° C./0.13 mbar and $n_D^{25} = 1.4972$, are obtained.

EXAMPLES 40 to 43

The following compounds are obtained similarly to Example 39:

TABLE 6

| | Parts of starting material III $Cl-\overset{O}{\overset{\|}{C}}-N=C\overset{Cl}{\diagdown_{Cl}}$ | Starting material II Parts of RNHSO$_2$Cl | | Parts of pyridine | Parts of end product I $\underset{O=\overset{\|}{C}-N=C\diagdown_{Cl}}{\overset{R\diagdown_{N}\diagup SO_2Cl}{}}\diagup^{Cl}$ | b.p. (°C./mbar) | $n_D^{25}$ | Yield (% of theory) |
|----|------|------|--------|------|------|------------|--------|------|
| 40 | 32.2 | 25.8 | CH$_3$ | 15.8 | 36.1 | 75–82/0.02 | 1.5038 | 71.2 |
| 41 | 32.2 | 28.7 | C$_2$H$_5$ | 15.8 | 37.5 | 68–75/0.02 | 1.4968 | 70.1 |
| 42 | 32.2 | 31.5 | C$_3$H$_7$(i) | 15.8 | 39.1 | 66/0.02 | 1.4981 | 69.4 |
| 43 | 32.2 | 34.3 | C$_4$H$_9$(n) | 15.8 | 34.2 | 88–95/0.02 | 1.4929 | 57.8 |

EXAMPLE 44 (USE EXAMPLE)

(a) 6 parts of isopropylamine in 50 parts of ether are added in portions to 19.9 parts of N-carbonylisocyanato-N-methyl-sulfamic acid chloride, from Example 2, in 150 parts of ether at from −50° C. to −55° C. The whole of the reaction mixture is then heated to room temperature, and the precipitate formed is filtered off, treated with ice water and again filtered off. 14 parts (54% of theory) of N-isopropyl-N'-(N''-methyl-N''-chlorosulfonyl)-carbamidourea of melting point 100°–105° C. are obtained.

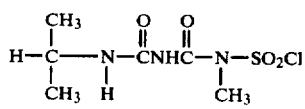

(b) The herbicidal activity of the end product of Example (44a) is ascertained in greenhouse experiments.

The containers used are plastic flowerpots of 300 cm$^3$ capacity, filled with loamy sand containing about 1.5% of humus. The seeds of the test plants, segregated according to species, are sown shallow. In the case of the pre-emergence treatment, the active ingredient is applied to the soil surface immediately thereafter, by suspending or emulsifying it in paraffin oil as the dispersing medium and spraying the suspension or emulsion onto the soil by means of atomizing nozzles. The amount applied is in each case 3.0 kg of active ingredient/ha. After application of the active ingredient, the pots are lightly sprinkled so as to stimulate germination and growth of the plants and at the same time to activate the chemical agents. The pots are then covered with transparent plastic covers until the plants have taken root. This cover ensures uniform germination of the test plants.

For post-emergence treatment, the plants are first grown in the test pots to a height of from 3 to 10 cm, depending on their growth habit, and are then treated. Here again the dose is 3 kg of active ingredient/ha. The pots are not covered. The experiments are carried out in a greenhouse, using the warmer parts of the greenhouse (25°–40° C.) for heat-loving species and using 15°–30° C. for temperate-zone plants. The test period is 3–6 weeks.

During this time, the plants are tended and their reaction to the individual treatments is evaluated on a scale from 0 to 100, 0 denoting no damage or normal germination and 100 denoting no germination of the plants or complete destruction of at least the visible parts of the shoots.

The test shows that the end product I from Example (44a), in pre-emergence use, exhibits a herbicidal action on wild oats (Avena fatua) as an example of graminaceous plants. In postemergent use, annual Italian ryegrass (Lolium multiflorum) and species of morning-glory (Ipomoea spp.)—the latter being an example of broad-leaved undesired plants—are severely damaged.

We claim:

1. A sulfamic acid halide of the formula $$\begin{array}{c} R^1 \\ \diagdown \\ \diagup N-SO_2Y \\ R^2 \end{array}$$

wherein,

R$^1$ is a straight or branched alkyl of 1–20 carbons being unsubstituted or substituted by halogen, or a cycloalkyl of 4–8 carbons;

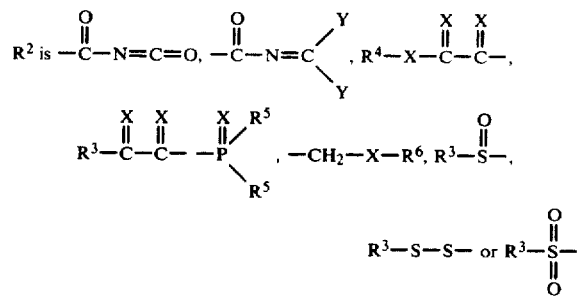

R$^3$ and R$^4$ are each an alkyl of 1–20 carbons being unsubstituted or substituted by 1 or 2 halogen atoms, 1 or 2 alkoxy groups of 1–4 carbons or combination thereof, a straight or branched alkenyl or alkynyl of 2–20 carbons being unsubstituted or substituted by 1 or 2 halogen atoms, 1 or 2 alkoxy groups of 1–4 carbons or combination thereof, a cycloalkyl of 4–8 carbons being unsubstituted or substituted by a chlorine atom, an aralkyl or alkylaryl of 7–12 carbons being unsubstituted or substituted by 1 or 2 halogen atoms, 1 or 2 nitro groups, 1 or 2 alkoxy groups of 1–3 carbons or combination thereof, an aryl of 6–12 carbons being unsubstituted or substituted by 1 or 2 halogen atoms, 1 or 2 nitro groups, 1 or 2 alkoxy groups of 1–3 carbons or combination thereof, a heterocyclic radical having 5 or 6 members containing 1 or 2 nitrogen atoms, an oxygen atom or combination thereof being unsubstituted or substituted by 1 or 2 halogen atoms, 1 or 2 nitro groups, 1 or 2 alkoxy groups of 1–3 carbons or combination thereof;

$R^3$ may also be F or Cl;
$R^5$ is Cl, —X—$R^6$ or —$R^6$;
$R^6$ is an alkyl of 1–20 carbons;
X is O or S;
Y is Cl or if $R^2$ is

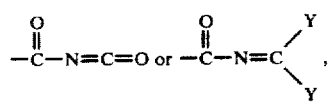

then Y is halogen, and any of the above listed alkyl, cycloalkyl, alkenyl, alkynyl, aralkylaryl, alkylaryl, or heterocyclic radicals may also be substituted with an alkyl of 1–4 carbons, a carbalkoxy of 2–4 carbons or a chlorocarbonyl, with the proviso that when $R^2$ is —$CH_2$—X—$R^6$, then $R^1$ is alkyl or cycloalkyl as defined above which are halogen free in the β-position to the nitrogen and X is S; when $R^2$ is

then $R^1$ is a cycloalkyl of 4–8 carbons or an alkyl of 1–20 carbons substituted by halogen.

2. A process for the preparation of a sulfamic acid halide of the formula

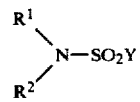

wherein, $R^1$ is a straight or branched alkyl of 1–20 carbons being unsubstituted or substituted by halogen, or a cycloalkyl of 4–8 carbons;

$R^2$ is

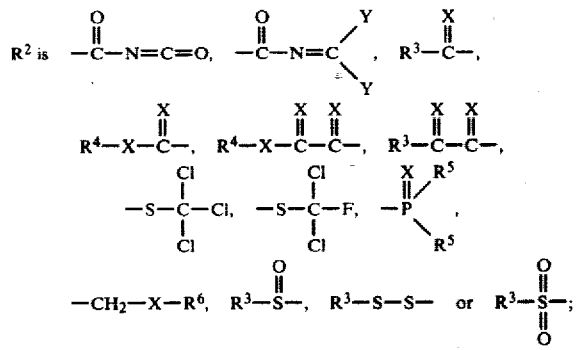

$R^3$ and $R^4$ are each an alkyl of 1–20 carbons being unsubstituted or substituted by 1 or 2 halogen atoms, 1 or 2 alkoxy groups of 1–4 carbons or combination thereof, a straight or branched alkenyl or alkynyl of 2–20 carbons being unsubstituted or substituted by 1 or 2 halogen atoms, 1 or 2 alkoxy groups of 1–4 carbons or combination thereof, a cycloalkyl of 4–8 carbons being unsubstituted or substituted by a chlorine atom, an aralkyl or alkylaryl of 7–12 carbons being unsubstituted or substituted by 1 or 2 halogen atoms, 1 or 2 nitro groups, 1 or 2 alkoxy groups of 1–3 carbons or combination thereof, an aryl of 6–12 carbons being unsubstituted or substituted by 1 or 2 halogen atoms, 1 or 2 nitro groups, 1 or 2 alkoxy groups of 1–3 carbons or combination thereof, or a heterocyclic radical having 5 or 6 members containing 1 or 2 nitrogen atoms, an oxygen atom or combination thereof being unsubstituted or substituted by 1 or 2 halogen atoms, 1 or 2 nitro groups, 1 or 2 alkoxy groups of 1–3 carbons or combination thereof;

$R^3$ may also be F or Cl;
$R^5$ is Cl, —X—$R^6$ or —$R^6$;
$R^6$ is an alkyl of 1–20 carbons;
X is O or S;
Y is Cl of if $R^2$ is

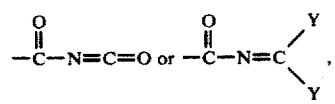

then Y is halogen; and any of the above listed alkyl, cycloalkyl, alkenyl, alkynyl, aryl, aralkyl, alkylaryl, or heterocyclic radicals may also be substituted with an alkyl of 1–4 carbons, a carbalkoxy of 2–4 carbons or a chlorocarbonyl, by reacting a sulfamic acid halide having the formula $R^1$—NH—$SO_2Y$ where $R^1$ and Y have the above meanings with a halogen compound having the formula $R^2$—Y where $R^2$ and Y have the above meanings in the presence of from 1 to 1.5 equivalents of a basic compound per mole of $R^2$—Y and in the presence of an inert, organic solvent, and, the resulting reaction mixture is subsequently treated with water at a pH of at most 7.

3. The process of claim 2, wherein the reaction is carried out with from 1 to 1.5 moles of starting material III per mole of starting material II.

4. The process of claim 2, wherein the reaction is carried out at from −50° to +80° C.

5. The process of claim 2, wherein the reaction is carried out at from −10° to +40° C.

6. The process of claim 2, wherein the reaction is carried out with starting materials III, where $R^2$ is

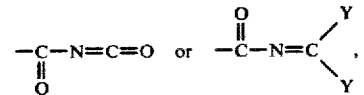

at from −50° to +70° C.

7. The process of claim 2, wherein the reaction is carried out in the presence of an organic solvent which is inert under the reaction conditions.

8. The process of claim 2, wherein the reaction mixture, or its filtrate, is treated with water for from 2 to 30 minutes at from 0° to 30° C. and at a pH of from 1 to 7.

* * * * *